(12) United States Patent
Davis

(10) Patent No.: US 7,265,136 B1
(45) Date of Patent: Sep. 4, 2007

(54) SUBSTITUTED STILBENE COMPOUNDS WITH VASCULAR DAMAGING ACTIVITY

(75) Inventor: Peter David Davis, Watlington (GB)

(73) Assignee: Angiogene Pharmaceuticals Ltd., Oxfordshire (GB)

( * ) Notice: Subject to any disclaimer, the term of this patent is extended or adjusted under 35 U.S.C. 154(b) by 0 days.

(21) Appl. No.: 09/890,990

(22) PCT Filed: Feb. 15, 2000

(86) PCT No.: PCT/GB00/00503

§ 371 (c)(1),
(2), (4) Date: Oct. 22, 2001

(87) PCT Pub. No.: WO00/48590

PCT Pub. Date: Aug. 24, 2000

(30) Foreign Application Priority Data

Feb. 16, 1999 (GB) ................................. 9903403.5

(51) Int. Cl.
*A61K 31/44* (2006.01)
*C07D 213/72* (2006.01)

(52) U.S. Cl. .................. 514/352; 546/304; 564/17; 564/26; 564/225; 562/439; 562/440; 560/19; 514/534; 514/585; 514/631

(58) Field of Classification Search ................ 514/534, 514/585, 631, 352; 564/26, 17, 225; 562/440, 562/439; 546/304; 560/19
See application file for complete search history.

(56) References Cited

FOREIGN PATENT DOCUMENTS

| EP | 0641767 | 3/1995 |
|---|---|---|
| WO | 92/16486 | 10/1992 |

OTHER PUBLICATIONS

Ohsumi, Koji, et al. "Novel Combretastain Analogues Effective against Murine Solid Tumors: Design and Structure-Activity Relationships" J. Med. Chem. (1998) vol. 41, No. 16 pp. 3022-3032.
Ohsumi, Koji, et al. "Syntheses and Antitumor Activity of Cis-Restricted Combretastatins: 5-Membered Heterocyclic Analogues." Bioorg. Med. Chem. Lett 8 (1998) pp. 3153-3158.
Pettit, George R., et al. "Antineoplastic agents 322. Synthesis of Combretastatin A-4 prodrugs" Anti-Cancer Drug Design (1995) vol. 10, No. 4 pp. 299-309.
Folkman, Judah, "Clinical Applications of Research on Angiogenesis" Seminars in Medicine of the Beth Israel Hospital, Boston (1995) vol. 333 No. 26 pp. 1757-1763.
Dark, Graham G., et al. "Combretastatin A-4, an Agent That Displays Potent and Selective Toxicity toward Tumor Vasculature[1]" Cancer Research (1997) vol. 57 pp. 1829-1834.
Chinje, E.C., et al., "Role of nitric oxide in growth of solid tumours: a balancing act" *Essays in Biochemistry*, vol. 32, pp. 61-72 (1997).

*Primary Examiner*—Charanjit S. Aulakh
(74) *Attorney, Agent, or Firm*—Ladas and Parry LLP

(57) ABSTRACT

A compound for use in inducing necrosis in vascular tissue of a tumor in an animal. The compound contains a first moiety which is a cis-stilbene moiety and a second moiety which is an inhibitor of the formation or action of nitric acid. Also, a method for inducing necrosis in vasculature of a tumor in an animal by administering to the animal the compound in an amount effective for inducing the necrosis.

17 Claims, No Drawings

SUBSTITUTED STILBENE COMPOUNDS WITH VASCULAR DAMAGING ACTIVITY

This invention relates to vascular damaging agents and particularly to a series of novel stilbene compounds.

Formation of new vasculature by angiogenesis is a key pathological feature of several diseases (J Folkman, New England Journal of Medicine 333, 1757-1763, 1995). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy. In all these diseases reversal of neovascularisation by damaging the newly-formed vascular endothelium is expected to have a beneficial therapeutic effect.

Combretastatin A4 phosphate is an agent known to have vascular damaging activity in animal models of solid tumours (Dark et al, Cancer Research 57, 1829-1834, 1997). However some tumours are resistant to this agent and doses approaching the maximum tolerated dose are necessary to produce significant vascular damage in these tumours.

One characteristic of tumours resistant to combretastatin A4 phosphate is their ability to produce large amounts of nitric oxide. The role of nitric oxide in tumour growth is unclear and there have been reports of both tumour-stimulating and tumour-inhibiting effects (Chinje and Stratford, Essays Biochem. 32, 61-72, 1997).

The present invention concerns novel combretastatin derivatives, methods for their preparation, pharmaceutical compositions containing them and their use as vascular damaging agents for the treatment of diseases involving active angiogenesis. These derivatives are more active than combretastatin A4 phosphate, particularly on tumours that are resistant to the known vascular damaging agents. In solid tumours vascular damaging agents exert their anti-tumour effect largely by inducing necrosis in the tumour, through starvation of the tumour's blood supply. Compounds of the invention show improved activity in the induction of necrosis in solid tumours. Though not limiting on the invention it is believed that the ability of compounds of the invention to reduce the production of nitric oxide during vascular damage by inhibition of one or more of the enzymes that produce nitric oxide (the nitric oxide synthases), is one way in which the compounds achieve increased activity.

Thus in one embodiment of the invention there is provided a compound of formula IA

A-X-B          IA

Wherein

A is a substituted cis-stilbene moiety

X is a linker bond, atom or group

B is a moiety derived from an inhibitor of the formation or action of nitric oxide in mammalian systems and the hydrates, pharmaceutically acceptable salts and prodrugs thereof.

In a more specific embodiment of the invention there is provided a vascular damaging agent which is a compound of formula I

A-X-B          I

Wherein

A is a substituted cis-stilbene moiety

X is a linker bond, atom or group

B is a moiety derived from an inhibitor of nitric oxide synthase and the hydrates, pharmaceutically acceptable salts and prodrugs thereof.

The linker X can be attached to any available atom of the stilbene moiety A and to any available atom of nitric oxide synthase inhibitor B as appropriate.

The stilbene moiety A can be for example a group of formula II

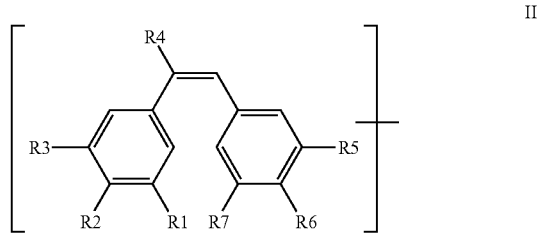

Wherein

R1, R2 and R3 are each independently H, optionally substituted alkoxy, optionally substituted alkyl or halogen R4 is hydrogen or cyano R5, R6 and R7 are each independently H, hydroxy, optionally substituted alkoxy, optionally substituted alkyl, halogen, amino, alkylamino, dialkylamino, cyano, nitro, carboxyl, alkanoyl, alkoxycarbonyl, alkoxycarbonyloxy, alkoxycarbonylamino, aminocarbonylamino, alkylaminocarbonylamino, dialkylaminocarbonylamino, alkylcarbonylamino, alkylsulphonyl, aminosulphonyl, alkylaminosulphonyl, dialkylaminosulphonyl, alkylsulphonylamino, aminosulphonylamino, alkylaminosulphonylamino, dialkylaminosulphonylamino, mercapto, alkylsulphanyl or alkylsulphinyl, with the proviso that at least two of R1, R2 and R3 must be optionally substituted alkoxy.

Stilbene moiety A can be attached to linker group X by any available valency.

Linker group X can be for example a bond, an optionally substituted methylene chain, or —(CH$_2$)$_m$—Y—(CH$_2$)$_n$— wherein Y is selected from —O—, —S—, —S(O)—, —SO$_2$—, —NH—, -Nalkyl-, —CO—, —OC(O)—, —NHC(O)—, —N(alkyl)C(O)—, —NHC(O)NH—, -NalkylC(O)NH—, -NalkylC(O)Nalkyl-, —NHSO$_2$—, -NalkylSO$_2$—, —NHSO$_2$NH—, -NalkylSO$_2$NH—, -NalkylSO$_2$Nalkyl- and —OC(O)O—, m is 0-3 and n is 0-3. Where the group Y is not symmetrical it can be oriented in either direction such that either end can be attached to the group A.

The nitric oxide synthase inhibitor moiety B can be a group derived from an inhibitor of nitric oxide synthase. Such inhibitors include, for example a group derived from an amino acid inhibitor of nitric oxide synthesis for example a group —C(O)CH(NH$_2$)—(CH$_2$)p—NHC(NH)Z wherein p is 1-5 and Z is alkyl, alkylamino, dialkylamino, nitroamino, hydrazino or alkylthio, or for example a group —NHCH(CO$_2$R10)—(CH$_2$)p—NHC(NH)Z where p and Z are as hereinbefore described and R10 is hydrogen or alkyl.

A further example of a nitric oxide synthase inhibitor moiety B is a group derived from thiocitrulline for example a group —C(O)CH(NH$_2$)—(CH$_2$)p—NHC(S)NH$_2$ or a group —NHCH(CO$_2$R10)—(CH$_2$)p—NHC(S)NH$_2$. A further example of a nitric oxide synthase inhibitor moiety B is a group derived from an S-alkylisothiourea for example —(CH$_2$)p—SC(NH)NH$_2$. A further example of a nitric oxide synthase inhibitor moiety B is a group derived from a 2-aminopyridine for example a 4-methyl-2-pyridinylamino group.

As used herein the term "alkyl", alone or in combinations, means a straight or branched-chain alkyl group containing from one to seven, preferably a maximum of four, carbon atoms such as methyl, ethyl, propyl, isopropyl, butyl, sec-butyl, t-butyl and pentyl. Examples of alkoxy groups are methoxy, ethoxy, propoxy, isopropoxy, butoxy and t-butoxy. The term "halogen" means fluorine, chlorine, bromine or iodine.

Optionally substituted alkoxy groups, optionally substituted alkyl groups and optionally substituted methylene chains may bear one or more substituents independently selected from halogen, hydroxy, amino, alkylamino, dialkylamino, carboxyl, mercapto, alkoxycarbonyl, aminocarbonyl, alkylaminocarbonyl, dialkylaminocarbonyl, alkylcarbonylamino, alkylcarbonyl(alkyl)amino, sulphate and phosphate.

One group of preferred compounds are those of formula III

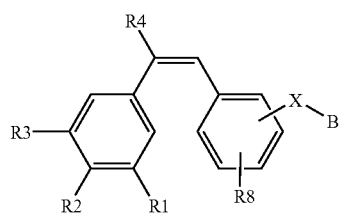

III

Wherein

R1, R2, R3, R4, X and B are as hereinbefore described

R8 is alkyl, amino, hydroxy, alkoxy or halogen

A further preferred group of compounds are those of formula III wherein R1, R2, R3, R4, are as hereinbefore described, R8 is alkyl, amino, hydroxy, alkoxy or halogen, X is —O— or —NH— and B is a group —C(O)CH(N$_2$)—(CH$_2$)p—NHC(N)Z wherein p is 1-5 and Z is alkyl, alkylamino, dialkylamino, nitroamino, hydrazino of alkylthio or a group —NHCH(CO$_2$R10)—(CH$_2$)p—NHC(NH)Z where p, Z and R10 are as hereinbefore described.

A still further preferred subset includes compounds of formula IV

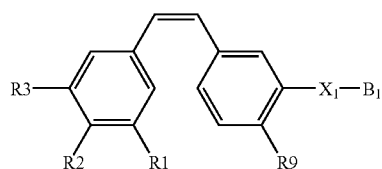

IV

Wherein

R1, R2 and R3 are as hereinbefore described

R9 is alkyl, alkoxy or halogen

X$_1$ is O or NH

B$_1$ is a group —C(O)CH(NH$_2$)—(CH$_2$)p—NHC(NH)Z wherein p is 1-5 and Z is alkyl, alkylamino, dialkylamino, nitroamino, hydrazino or alkylthio.

Particularly preferred compounds include:
(Z)-1-(4-Methoxy-3-N$^G$-nitroarginyloxyphenyl)-2-(3,4,5-trimethoxyphenyl)ethene
(Z)-N-[2-methoxy-5-[2-(3,4,5-trimethoxyphenyl)ethenyl]phenoxycarbonyl]N$^G$-nitroarginine methyl ester
(Z)-N-[2-methoxy-5-[2-(3,4,5-trimethoxyphenyl)ethenyl]phenoxycarbonyl]N$^G$-nitroarginine
(Z)-N-[2-methyl-5-[2-(3,4,5-trimethoxyphenyl)ethenyl]phenoxycarbonyl]N$^G$-nitroarginine methyl ester For the avoidance of doubt it is to be understood that where in this specification a group is qualified by "hereinbefore defined" or "defined hereinbefore", or "hereinafter defined" or "defined hereinafter", the said group encompasses the first occurring and broadest definition as well as each and all of the preferred definitions for that group.

Where one or more functional groups in compounds of formula I are sufficiently basic or acidic the formation of salts is possible. Suitable salts include pharmaceutically acceptable salts for example acid addition salts including hydrochlorides, hydrobromides, phosphates, sulphates, hydrogen sulphates, alkylsulphonates, arylsulphonates, acetates, benzoates, citrates, maleates, fumarates, succinates, lactates and tartrates, salts derived from inorganic bases including alkali metal salts such as sodium or potassium salts, alkaline earth metal salts such as magnesium or calcium salts, and salts derived from organic amines such as morpholine, piperidine or dimethylamine salts.

Compounds of formula I or IA or a salt thereof may exhibit tautomerism and the formulae drawings within this specification represent only one of the possible tautomeric forms. It is to be understood that the invention encompasses any tautomeric form that has vascular damaging activity and is not to be limited merely to any one tautomeric form utilised within the formulae drawings.

Those skilled in the art will recognise that compounds of formula I or IA may exist as stereoisomers and accordingly the present invention includes all such isomers and mixtures thereof which have vascular damaging activity. Where the group derived from a nitric oxide synthase inhibitor is derived from an amino acid inhibitor of nitric oxide synthase the L-configuration of the amino acid is preferred.

Compounds of the invention can be prepared by any process known to a person skilled in the art. Compounds of formulae IA, I, III and IV can be prepared by a number of processes as generally described hereinbelow and more specifically in the Examples hereinafter. In the general preparations described below it may be necessary to employ protecting groups which are then removed during the final stages of the synthesis. The appropriate use of such protecting groups and processes for their removal will be readily apparent to those skilled in the art. In the following process description, the symbols R1, R2, R3, R4, R5, R6, R7, X and B when used in the formulae depicted are to be understood to represent those groups described above in relation to formula I unless otherwise indicated Thus according to a further aspect of the invention compounds of the invention may be prepared by attachment of a nitric oxide synthase inhibitor to a stilbene of formula V using alkylation, acylation, sulphonylation or coupling reactions. Alternatively stilbenes of formula V may be coupled to a difunctional compound (which provides the linker group —X—) and further coupled to the nitric oxide inhibitor via the remaining functionality on the linker group as appropriate. Stilbenes of formula V are either known or can be prepared using methods analagous to those used in the preparation of the known stilbenes which will be apparent to those skilled in the art.

In one general example compounds of formulae I can be prepared from a stilbene of formula V containing a free OH or NH by acylation with a nitric oxide synthase inhibitor containing a carboxylic acid for example using a coupling agent such as a carbodiimide, for example dicyclohexylcarbodiimide, or 1-(3-dimethylaminopropyl)-3-ethylcarbodiimide and, optionally, a base such as an organic base for example triethylamine and, optionally, a catalyst such as 4-dimethylaminopyridine in a solvent such as an aprotic solvent for example dimethylformamide or in a chlorinated solvent for example chloroform or dichloromethane at a temperature in the range from about −30° C. to about 60° C., conveniently at or near room temperature.

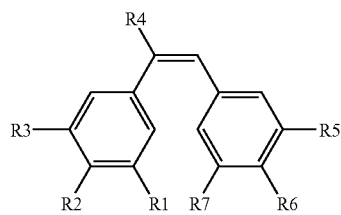

V

In another general example a compound or formula V containing a free OH or NH group can be treated with 4-nitrophenylchloroformate in a solvent such as pyridine at a temperature of about −10° C. to room temperature followed by treatment with a nitric oxide synthase inhibitor containing a free OH or NH group to give a compound of formula I containing a carbonate, carbamate or urea group.

In another general example a compound of formula V containing a free NH group can be treated with a dicarboxylic acid monoester such as monomethyl succinate in the presence of a coupling agent such as a carbodiimide, for example dicyclohexylcarbodiimide, or 1-(3-dimethylaminopropyl)-3-ethylcarbodimide and, optionally, a base such as an organic base for example triethylamine in a solvent such as an aprotic solvent for example dimethylformamide or in a chlorinated solvent for example chloroform or dichloromethane at a temperature in the range from about −30° C. to about 60° C., conveniently at or near room temperature. The resulting ester can be hydrolysed by treatment with aqueous acid or aqueous base under standard conditions and the carboxylic acid so obtained treated with a nitric oxide inhibitor containing a free OH or NH group, using a coupling agent as described hereinbefore, to give compounds of the invention.

In another general example a compound of formula V containing a carboxylic acid group can be converted into a compound of formula I containing an amide or ester by treatment with a nitric oxide synthase inhibitor, containing an amino group or a hydroxyl group respectively, using a coupling agent as described hereinbefore.

In another general example a compound of formula V containing a monohaloalkyl group can be reacted with a nitric oxide synthase inhibitor containing a free OH, NH, or SH group in the presence of a base such as sodium carbonate or a metal hydride such as sodium hydride in a solvent such as dimethylformamide at a temperature of about 0° C. to a temperature of about 100° C. to give compounds of the invention.

In another general example a compound of formula V containing a carboxylic acid group can be treated with a monoprotected diamino, dihydroxy or aminohydroxy compound such as a monoprotected diaminoalkane, a monoprotected dihydroxyalkane or mono-protected aminohydroxyalkane, using a coupling agent as described hereinbefore and the resulting amide or ester deprotected and reacted with a nitric oxide synthase inhibitor containing a carboxylic acid using a coupling agent as described hereinbefore.

In another general example a compound of formula V containing a free OH or NH group can be sulphonylated with a protected amino sulphonylchloride such as a protected aminoalkylsulphonylchloride or a protected hydroxy sulphonyl chloride such as a protected hydroxyalkylsulphonyl chloride, in the presence of a base, for example a tertiary amine base such as triethylamine, in for example a solvent such as a hydrocarbon solvent e.g. dichloromethane at a temperature in the range for example −30° C. to 120° C., conveniently at or near ambient temperature and the resulting sulphonamide or sulphonate deprotected and reacted with a nitric oxide synthase inhibitor containing a carboxylic acid using a coupling agent as described hereinbefore.

In another general example a compound of formula V containing a free OH, SH or NH group can be alkylated with a difunctional alkylating agent such as a dihaloalkane in the presence of a base such as sodium carbonate or a metal hydride such as sodium hydride in a solvent such as dimethylformamide at a temperature of about 0° C. to a temperature of about 100° C., and the resulting haloalkane further reacted under similar conditions with a nitric oxide synthase inhibitor containing a free OH, SH or NH group.

Compounds of formula VII can also be prepared by Wittig olefin synthesis involving reaction of a phosphonium salt of formula VI with a strong base, for example an alkyllithium such as n-butyllithium or t-butyllithium or a metal hydride such as sodium hydride in a solvent such as an ether solvent for example diethyl ether or tetrahydrofuran or in a solvent such as a hydrocarbon solvent for example toluene at a temperature of between about −100° C. to about 30° C. followed by treatment with an aldehyde of formula VII.

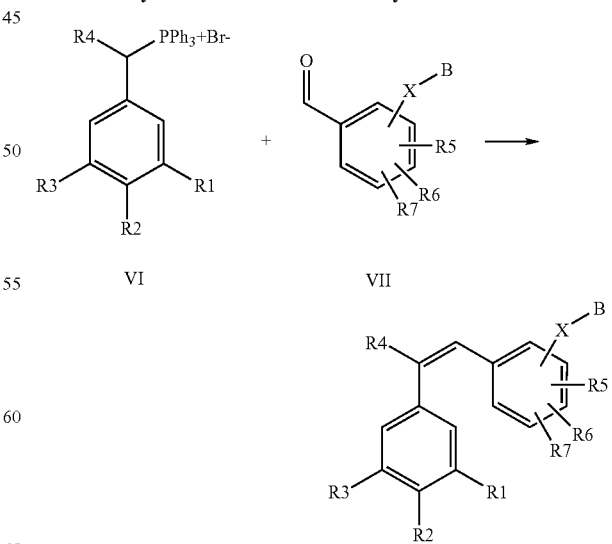

Compounds of formula I can also be prepared from other compounds of formula I by chemical modification. Examples of such chemical modifications that may be applied are standard alkylation, acylation, thioacylation, sulphonylation, aromatic halogenation and coupling reactions. These reactions may be used to add new substituents or to modify existing substituents. Alternatively, existing substituents in compounds of formula I may be modified by, for example, oxidation, reduction, elimination, hydrolysis or other cleavage reaction to yield other compounds of formula I.

Thus for example a compound of formula I containing an amino group may be acylated on the amino group by treatment with, for example, an acyl halide or anhydride in the presence of a base, for example a tertiary amine base such as triethylamine, in for example, a solvent such as a hydrocarbon solvent e.g. dichloromethane at a temperature in the range for example −30° C. to 120° C., conveniently at or near ambient temperature.

In another general example of an interconversion process an amino group in a compound of formula I may be sulphonylated by treatment with, for example, an alkyl or aryl sulphonyl chloride or an alkyl or aryl sulphonic anhydride in the presence of a base, for example a tertiary amine base such as triethylamine, in for example a solvent such as a hydrocarbon solvent e.g. dichloromethane at a temperature in the range for example −30° C. to 120° C., conveniently at or near ambient temperature.

In a further general example a compound of formula 1 containing an ester can be hydrolysed by treatment with an acid, for example sulphuric acid, in a solvent such as tetrahydrofuran in the presence of water at a temperature of about room temperature to the reflux temperature of the solvent, preferably at or around 60° C.

In a further general example a compound of formula I containing an amide can be hydrolysed by treatment with for example an acid such as hydrochloric acid in a solvent such as an alcohol, for example methanol at an elevated temperature conveniently at the reflux temperature.

In another general example an O-alkyl group may be cleaved to the corresponding alcohol (OH) by reaction with boron tribromide in a solvent such as a chlorinated solvent e.g. dichloromethane at a low temperature e.g. around −78° C.

In a further general example compounds of formula I may be alkylated by reaction with a suitable alkylating agent such as an alkyl halide, an alkyl toluenesulphonate, an alkyl methanesulphonate or an alkyl triflate. The alkylation reaction can be carried out in the presence of a base for example an inorganic base such as a carbonate e.g. caesium or potassium carbonate, a hydride such as sodium hydride or an alkoxide such as potassium t-butoxide in a suitable solvent such as an aprotic solvent e.g. dimethylformamide or an ether solvent such as tetrahydrofuran at a temperature of around −10 to 80° C.

Preparation of a compound of formula I as a single enantiomer or, where appropriate, diastereomer may be effected by synthesis from an enantiomerically pure starting material or intermediate or by resolution of the final product in a conventional manner.

Acid addition salts of the compounds of formula I are prepared in a conventional manner by treating a solution or suspension of the free base I with about one equivalent of a pharmaceutically acceptable acid. Salts of compounds of formula I derived from inorganic or organic bases are prepared in a conventional manner by treating a solution or suspension of the free acid I with about one equivalent of a pharmaceutically acceptable organic or inorganic base. Alternatively both acid addition salts and salts derived from bases may be prepared by treatment of the parent compound with the appropriate ion-exchange resin in a standard fashion. Conventional concentration and recrystallisation techniques are employed in isolating the salts.

Compounds according to the invention are able to destroy tumour vasculature and vasculature that has been newly formed while leaving unaffected normal, mature vasculature. The ability of the compounds to act in this way may be determined by the tests described in the Examples hereinafter.

The compounds according to the invention are thus of particular use in the prophylaxis and treatment of cancers involving solid tumours and in the prophylaxis and treatment of diseases where inappropriate angiogenesis occurs such as diabetic retinopathy, psoriasis, rheumatoid arthritis, atherosclerosis and macular degeneration.

The compounds of the invention may be administered as a sole therapy or in combination with other treatments. For the treatment of solid tumours compounds of the invention may be administered in combination with radiotherapy or in combination with other anti-tumour substances for example those selected from mitotic inhibitors, for example vinblastine, paclitaxel and docetaxel; alkylating agents, for example cisplatin, carboplatin and cyclophosphamide; antimetabolites, for example 5-fluorouracil, cytosine arabinoside and hydroxyurea; intercalating agents for example adriamycin and bleomycin; enzymes, for example aspariginase; topoisomerase inhibitors for example etoposide, topotecan and irinotecan; thymidylate synthase inhibitors for example raltitrexed; biological response modifiers for example interferon; antibodies for example edrecolomab; and anti-hormones for example tamoxifen. Such combination treatment may involve simultaneous or sequential application of the individual components of the treatment.

For the prophylaxis and treatment of disease the compounds according to the invention may be administered as pharmaceutical compositions selected with regard to the intended route of administration and standard pharmaceutical practice. Such pharmaceutical compositions may take a form suitable for oral, buccal, nasal, topical, rectal or parenteral administration and may be prepared in a conventional manner using conventional excipients. For example for oral administration the pharmaceutical compositions may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion.

The dose of a compound of the invention required for the prophylaxis or treatment of a particular condition will vary depending on the compound chosen, the route of administration, the form and severity of the condition and whether the compound is to be administered alone or in combination with another drug. Thus the precise dose will be determined by the administering physician but in general daily dosages may be in the range 0.001 to 100 mg/kg preferably 0.01 to 50 mg/kg.

Biological Activity

The following test was used to demonstrate the activity of compounds according to the invention:

Activity Against Tumour Vasculature Measured by Fluorescent Dye.

The following experiment further demonstrates the ability of the compounds to damage tumour vasculature.

Tumour functional vascular volume in CaNT tumour-bearing mice was measured using the fluorescent dye Hoechst 33342 according to the method of Smith et al (Brit J Cancer 57, 247-253, 1988). The fluorescent dye was dissolved in saline at 6.25 mg/ml and injected intravenously at 10 mg/kg 24 hours after drug treatment. One minute later, animals were killed and tumours excised and frozen; 10 μm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (J Natl Cancer Inst, 4, 47-53, 1943). All estimates were based on counting a minimum of 100 fields from sections cut at the 3 different levels.

Induction of Necrosis

Mice bearing either CaNT or SaS tumours were treated with the test compound and tumours excised after 24 h, fixed in formalin, embedded in paraffin, sectioned and stained with haematoxylin and eosin. Sections were scored based on area of necrosis as follows:

| % necrosis | score | % necrosis | score |
|---|---|---|---|
| 0-10 | 1 | 51-60 | 6 |
| 11-20 | 2 | 61-70 | 7 |
| 21-30 | 3 | 71-80 | 8 |
| 31-40 | 4 | 81-90 | 9 |
| 41-50 | 5 | 91-100 | 10 |

Control tumours had mean scores of 2.0 (CaNT) and 1.0 (SaS). Mean values from at least three different tumours were obtained for each test compound.

Table: Reduction in Vascular Volume and Induction of Necrosis in the Carcinoma NT Tumour 24 h Post Dose: Comparison with Combretastatin A4 phosphate (CA4P).

| Compound | Dose | Vascular volume % reduction | Necrosis score |
|---|---|---|---|
| CA4P | 50 mg/kg i.v. | 88 | 5.7 |
| CA4P | 50 mg/kg i.p. | 91 | 6.0 |
| Cmpd. of Example 1 | 50 mg/kg i.v. | 98 | 10.0 |
| Cmpd. of Example 2 | 50 mg/kg i.p. | 95 | 8.0 |

The following non-limiting Examples illustrate the invention:

EXAMPLE 1

(Z)-1-(4-Methoxy-3-$N^G$-nitroarginyloxyphenyl)-2-(3,4,5-trimethoxyphenyl)ethene Trifluoroacetic acid (0.2 ml) was added to a solution of (Z)-1-(3-(N-α-t-butoxycarbonyl-N-ω-nitroarginyloxy)-4-methoxyphenyl)-2-(3,4,5-trimethoxyphenyl)ethene (82 mg) in dichloromethane (3 ml) at 0° C. and the mixture allowed to come to room temperature and stir 16 h. The mixture was concentrated under reduced pressure, ethanol (5 ml) was added, the mixture was reconcentrated under reduced pressure and the procedure repeated three times. Trituration with diethyl ether afforded the title compound (69 mg) as an off-white powder m.p. 157-159° C.

The (Z)-1-(3-(N-α-t-butoxycarbonyl-N-ω)-nitroarginyloxy)-4-methoxyphenyl)-2-(3,4,5-trimethoxyphenyl)ethene used in the above procedure was prepared as follows: A solution of (Z)-1-(3-hydroxy-4-methoxyphenyl)-2-(3,4,5-trimethoxyphenyl)ethene (65 mg, 0.21 mmol), Nα-t-BOC-ω-nitro-L-arginine (134 mg, 0.42 mmol), 1-(3-dimethylaminopropyl)-3-ethylcarbodiimide hydrochloride (110 mg, 0.54 mmol) and 4-dimethylaminopyridine (5 mg) in dichloromethane (2.1 ml) was stirred at room temperature for 72 h. The reaction mixture was partitioned between dichloromethane and water and the aqueous phase extracted with two portions of dichloromethane. The combined organic extracts were washed successively with two portions of water and one of brine, dried (MgSO4) and concentrated under reduced pressure. The residue was chromatographed on silica gel eluting with 33% ethyl acetate/hexane followed by 100% ethyl acetate to give (Z)-1-(3-(N-α-t-butoxycarbonyl-N-ω-nitroarginyloxy)-4-methoxyphenyl)-2-(3,4,5-trimethoxyphenyl)ethene (82 mg) as a white oil.

EXAMPLE 2

(Z)-N-[2-methoxy-5-[2-(3,4,5-trimethoxyphenyl)ethenyl]phenoxycarbonyl]$N^G$-nitroarginine Methyl Ester A solution of (Z)-1-(3-hydroxy-4-methoxyphenyl)-2-(3,4,5-trimethoxyphenyl)ethene (400 mg, 1.27 mmol) in dry pyridine (2 ml) was added dropwise to a cooled (0° C.) mixture of 4-nitrophenylchloroformate (282 mg, 1.40 mmol) and dry pyridine (1 ml). After 20 min the reaction mixture was warmed to room temperature and stirred for a further 6 h. To this was added L-$N^G$-nitroarginine methyl ester hydrochloride (343 mg, 1.27 mmol, azeotroped with toluene) and the mixture heated (70° C.) for 72 h. After cooling to room temperature, the reaction mixture was partitioned (ethyl acetate, water), the organic layer was washed (water×3), the aqueous layer was extracted (ethyl acetate×3), the combined organic fractions were further washed (water×2, saturated $NaCl_{(aq)}$×1), dried ($MgSO_4$), and concentrated in vacuo. Flash silica chromatography, eluting with 50% ethyl acetate/hexane then 100% ethyl acetate, afforded the title compound as a white foam (292 mg). Elemental analysis: calculated C 54.26% H 5.78% N 12.17%, found C 53.97% H 6.07% N 11.55%.

EXAMPLE 3

(Z)-N-[2-methoxy-5-[2-(3,4,5-trimethoxyphenyl)ethenyl]phenoxyncarbonyl]$N^G$-nitroarginine A mixture of (Z)-N-[2-methoxy-5-[2-(3,4,5-trimethoxyphenyl)ethenyl]phenoxycarbonyl]$N^G$-nitroarginine methyl ester (95 mg, 0.165 mmol), tetrahydrofuran (10 ml), water (10 ml) and concentrated sulphuric acid (1 ml) were heated at 60° C. for 72 h. After cooling to room temperature, the reaction mixture was partitioned (ethyl acetate, water), the aqueous layer was extracted (ethyl acetate×3), the combined organic fractions were further washed (water×2, saturated $NaCl_{(aq)}$×1), dried ($MgSO_4$), and concentrated in vacuo. The title compound was obtained as an opaque oil (90 mg, 98%). LC-MS indicated purity>95%.

In a similar manner to Example 2 there was prepared:

EXAMPLE 4

(Z)-N-[2-methyl-5-[2-(3,4,5-trimethoxyphenyl)ethenyl]phenoxycarbonyl]N$^G$-nitroarginine Methyl Ester From (Z)-1-(3-hydroxy-4-methyl)-2-(3,4,5-trimethoxyphenyl)ethene (125 mg, 0.42 mmol), nitrophenylchloroformate (93 mg, 0.46 mmol) and L-N$^G$-nitroarginine methyl ester hydrochloride(13 mg, 0.42 mmol) there was obtained the title compound (15 mg) as a colourless oil. LC-MS indicated purity>95%. MS (m/z) 300 (M⁺), 285. The (Z)-1-(3-hydroxy-4-methyl)-2-(3,4,5-trimethoxyphenyl)ethene used as starting material was prepared as follows:

A suspension of 3,4,5-trimethoxybenzyltriphenylphosphonium bromide (8 g, 15.3 mmol) in tetrahydrofuran (450 ml) at −23° C. was treated with n-butyllithium (10 ml of a solution in hexanes, 15.3 mmol) dropwise and the mixture stirred for 1 h. 4-methoxy-3-tert-butyldimethylsilyloxybenzaldehyde (4.07 g, 15.3 mmol) was added and the mixture stirred a further 4 h at −23° C. before warming to room temperature and stirring a further 16 h. The mixture was poured on to ice-water (150 ml) and extracted with diethyl ether (three portions of 150 ml). The combined extracts were washed with water (three portions of 150 ml) and brine (150 ml), dried (MgSO4) and concentrated under reduced pressure. The residue was purified by chromatography on silica gel eluting with 5% ethyl acetate in hexane followed by 15% ethyl acetate in hexane to give a white solid (4.61 g) consisting of (Z)-1-(4-methyl-3-tert-butyldimethylsilyloxyphenyl)-2-(3,4,5-trimethoxyphenyl)ethene. A portion of this material (3.46 g, 8 mmol) was dissolved in tetrahydrofuran (60 ml) and treated with tetrabutylammonium fluoride (8.3 ml of a 1.0M solution in tetrahydrofuran, 8.3 mmol) and stirred for 20 min. Ice (20 g) was added and the mixture extracted with diethyl ether (200 ml). The extract was washed with water (three portions of 80 ml), dried (MgSO4) and concentrated under reduced pressure. The residue was purified by chromatography on silica gel eluting with 40% ethyl acetate in hexane. 1-(3-hydroxy-4-methyl)-2-(3,4,5-trimethoxyphenyl)ethene (2.01 g) was obtained as a white solid.

The invention claimed is:

1. A compound of formula AXB useful in inducing necrosis in vascular tissue of a tumor in a mammal, said compound containing (a) a first moiety, A, which is a cis-stilbene moiety of formula II

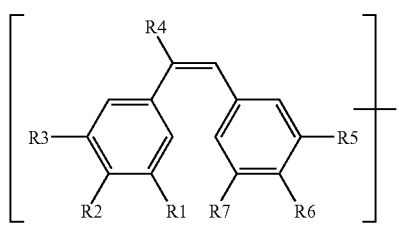

wherein R1, R2 and R3 are each independently H, optionally substituted alkoxy, optionally substituted alkyl or halogen
R4 is hydrogen or cyano
R5, R6 and R7 are each independently H, hydroxy, optionally substituted alkyl, halogen, amino, alkylamino, dialkylamino, cyano, nitro, carboxyl, alkanoyl, alkoxycarbonyl, alkoxycarbonylamino, aminocarbonylamino, alkylaminocarbonylamino, di alkylaminocarbonylamino, alkylcarbonylamino, alkylsulphonyl, aminosulphonyl, alkylaminosulphonyl, dialkylaminosulphonyl, alkylsulphonylamino, aminosulphonylamino, alkylaminosulphonylamino, dialkylaminosulphonylamino, mercapto, alkylsulphanyl, or alkylsulphinyl,
with the proviso that at least two of R1, R2 and R3 must be optionally substituted alkoxy, and (b) a second moiety, B, which is an inhibitor of nitric oxide synthase said first and second moieties being coupled in the compound by X which is a linker bond or moiety bound to any available valency of B and any available valency of that phenyl ring of Formula II that is substituted by R5, R6 and R7 such that the compound has an increased activity in inducing necrosis in said vascular tissue as compared with a compound containing said first moiety without the second moiety, wherein X is selected from the group consisting of an optionally substituted methylene chain and —(CH2)$_m$—Y—(CH2)$_n$ wherein Y is selected from —O—, —S—, —SO$_2$, NH—, N alkyl, —CO—, —OC(O)—, —NHC(O), —N(alkyl)C(O)—, NNHC( ))NH—, NalkylC(O)NH-NalkylC(O)Nalkyl, NHSO$_2$, NalkylSO$_2$—, NHSO$_2$NH, NalkylSO$_2$NH, NalkylSO$_2$Nalkyl and —OC(O)O, m is 0-3 and n is 0-3 or a hydrate or pharmaceutically acceptable salt of the compound.

2. The compound according to claim 1, wherein the compound is a hydrate, or a pharmaceutically acceptable salt thereof.

3. The compound according to claim 1, in which the second moiety is selected from the group consisting of an amino acid inhibitor of nitric oxide synthase, a thiocitrulline derivative, an S-alkylisothiourea derivative and a 2-aminopyridine derivative.

4. The compound according to claim 1, wherein the second moiety is a group —C(O)CH(NH$_2$)—CH$_2$p—NHC(NH)Z wherein p is 1-5 and Z is alkyl, alkylamino, dialkylamino, nitroamino, hydrazino or alkylthio, or a group —NHCH(CO$_2$R10)—(CH$_2$)p—NHC(NH)Z and R10 is hydrogen or alkyl.

5. The compound according to claim 1, wherein the second moiety is a group —C(O)CH(NH$_2$)—CH$_2$p—NHC(S)NH$_2$ or a group —NHCH(CO$_2$R10)—(CH$_2$)p—NHC(S)NH$_2$ wherein p is 1-5 and R10 is hydrogen or alkyl.

6. The compound according to claim 1, wherein the second moiety is —(CH$_2$)p—SC(NH)NH$_2$ wherein p is 1-5.

7. The compound according to claim 1, wherein the second moiety is 4-methyl-2-pyridinylamino.

8. The compound according to claim 1, wherein the compound is

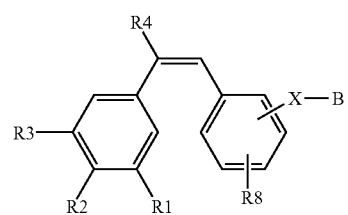

wherein R8 is alkyl, amino, hydroxy, alkoxy or halogen.

9. The compound according to claim 8, wherein X is —O— or —NH— and B is a group —C(O)CH(NH$_2$)—(CH$_2$)p—NHC(NH)Z, wherein p is 1-5 and Z is alkyl, alkylamino, dialkylamino, nitroamino, hydrazino or alkylthio or a group —NHCH(CO$_2$R10)—(CH$_2$)p—NHC(NH)Z and wherein R10 is hydrogen or alkyl.

10. The compound according to claim 9, wherein the compound is

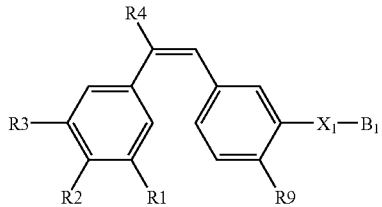

wherein
R9 is alkyl, alkoxy or halogen
X$_1$ is O or NH
B$_1$ is a group —C(O)CH(NH$_2$)p—NHC(NH)Z wherein p is 1-5 and Z is alkyl, alkylamino, dialkylamino, nitroamino, hydrazino or alkylthio.

11. The compound according to claim 1, wherein the compound is selected from the group consisting of
(Z)-1-(4-methoxy-3-N$^G$-nitroarginyloxyphenyl)-2-(3,4,5-trimethoxyphenyl)ethene (Z)-N-[2-methoxy-5-[2-(3,4,5-trimethoxyphenyl)ethenyl]phenoxycarbonyl]N$^G$-nitroarginine methyl ester;
(Z)-N-[2-methoxy-5-[2-(3,4,5-trimethoxyphenyl)ethenyl]phenoxycarbonyl]N$^G$-nitroarginine; and
(Z)-N-[2-methyl-5-[2-(3,4,5-trimethoxyphenyl)ethenyl]phenoxycarbonyl]N$^G$-nitroarginine methyl ester.

12. The compound according to claim 1, wherein the first and second moieties are coupled through a linker bond.

13. A method for inducing necrosis in vasculature of a tumor in a mammal, comprising administering to the mammal the compound of claim 11 in an amount effective for said inducing.

14. A method for inducing necrosis in vasculature of a tumor in a mammal, comprising administering to the mammal the compound of claim 1 in an amount effective for said inducing.

15. A method for inducing necrosis in vasculature of a tumor in a mammal, comprising administering to the mammal the compound of claim 12 in an amount effective for said inducing.

16. A method for inducing necrosis in vasculature of a tumor in a mammal, comprising administering to the mammal the compound of claim 4 in an amount effective for said inducing.

17. A method for inducing necrosis in vasculature of a tumor in a mammal, comprising administering to the mammal the compound of claim 8 in an amount effective for said inducing.

* * * * *